United States Patent
Scott et al.

(10) Patent No.: US 7,038,196 B2
(45) Date of Patent: May 2, 2006

(54) ACCELERATED WEATHERING TEST APPARATUS WITH FULL SPECTRUM CALIBRATION, MONITORING AND CONTROL

(75) Inventors: Kurt Scott, Chicago, IL (US); Christopher Waas, North Riverside, IL (US); Anatoliy Ivanov, Chicago, IL (US)

(73) Assignee: Atlas Material Testing Technology LLC, Chicago, IL (US)

( * ) Notice: Subject to any disclaimer, the term of this patent is extended or adjusted under 35 U.S.C. 154(b) by 58 days.

(21) Appl. No.: 10/770,174

(22) Filed: Feb. 2, 2004

(65) Prior Publication Data

US 2005/0167580 A1    Aug. 4, 2005

(51) Int. Cl.
*G01D 18/00* (2006.01)
*G12B 13/00* (2006.01)
*G01J 1/42* (2006.01)
*G01T 1/00* (2006.01)
*G01N 17/00* (2006.01)

(52) U.S. Cl. .................. 250/252.1; 250/393; 73/865.6

(58) Field of Classification Search ............. 250/338.1, 250/339.01, 339.05–339.07, 339.09, 393, 250/252.1, 205, 354.1; 356/51, 319–320; 315/149, 151, 156–158; 702/85, 865.6; 73/865.6
See application file for complete search history.

(56) References Cited

U.S. PATENT DOCUMENTS

| | | | |
|---|---|---|---|
| 3,870,873 A | 3/1975 | Mallory | |
| 3,996,494 A | 12/1976 | Suga | |
| 4,012,663 A | 3/1977 | Soileau | |
| 4,025,440 A | 5/1977 | Suga | |
| 4,391,522 A | * | 7/1983 | Schmid et al. .............. 356/326 |
| 4,618,776 A | 10/1986 | Sturm et al. | |
| 4,644,166 A | 2/1987 | Sturm et al. | |
| 4,825,078 A | 4/1989 | Huber et al. | |
| 4,922,089 A | 5/1990 | McGuire et al. | |
| 5,004,349 A | 4/1991 | Sato et al. | |
| 5,136,886 A | 8/1992 | Neigoff et al. | |
| 5,206,518 A | 4/1993 | Fedor et al. | |
| 5,226,318 A | 7/1993 | Huber et al. | |
| 5,340,974 A | 8/1994 | Zalewski | |

(Continued)

OTHER PUBLICATIONS

Schneider, W., and Young, R. "Spectroradiometry Methods: A Guide to Photometry and Visible Spectroradiometry". Application Note A14 [online]. Optronic Laboratories Inc., Jan. 1998 [retrieved on Jun. 9, 2005]. Continued in item V below.*

(Continued)

*Primary Examiner*—David Porta
*Assistant Examiner*—Frederick F. Rosenberger
(74) *Attorney, Agent, or Firm*—Vedder Price Kaufman & Kammholz

(57) ABSTRACT

An accelerated weathering test apparatus and method for calibration and operation thereof including a spectroradiometer for monitoring a full spectrum power distribution of a light source. Calibration includes a calibration light source in a factory test apparatus operated at a fixed power level and collecting the full spectrum power distribution of the calibration light source to generate a first data set. The calibration light source is then installed in a client test apparatus and operated at the fixed power level in order to collect the full spectrum power distribution and generate a second data set. The first and second data sets are filtered and aligned to determine a system response factor of the client test apparatus so that the irradiance level control may be calibrated.

41 Claims, 14 Drawing Sheets

U.S. PATENT DOCUMENTS

| | | |
|---|---|---|
| 5,488,267 A | 1/1996 | Rudolph et al. |
| 5,503,032 A | 4/1996 | Tikhtman et al. |
| 5,521,392 A | 5/1996 | Kennedy et al. |
| 5,854,433 A | 12/1998 | Patel et al. |
| 6,239,554 B1 * | 5/2001 | Tessadro et al. ............ 315/149 |
| 6,285,137 B1 | 9/2001 | Grossman et al. |
| 6,303,916 B1 | 10/2001 | Gladnick |
| 6,720,562 B1 * | 4/2004 | Rathod et al. .............. 250/395 |

OTHER PUBLICATIONS

Retrieved from the Internet: <URL: http://www.olinet.com/pdfs/A14_Spectroradiometry-Methods.pdf>.*

* cited by examiner

ACCELERATED WEATHERING TEST APPARATUS WITH FULL SPECTRUM CALIBRATION, MONITORING AND CONTROL

FIELD OF THE INVENTION

The present invention is directed to an accelerated weathering test apparatus and, more particularly, to an indoor accelerated weathering test apparatus which uses a full spectrum power distribution ("SPD") of an artificial light source for calibration, monitoring and control of the apparatus.

BACKGROUND OF THE INVENTION

Indoor accelerated weathering test apparatus are known to test the accelerated aging characteristics of painted surfaces, fabrics, plastic sheeting and other materials. Such testing is accomplished by exposing the materials to be tested to high intensity radiation from an artificial light source that approximates sunlight, under conditions of controlled and sometimes high temperature and/or humidity.

In a natural outdoor environment, heat, light and moisture combine to synergistically cause optical, mechanical and chemical changes in products which are exposed to such outdoor weathering conditions. Generally, the test apparatus of the present invention and the prior art can be used to obtain such weathering data on an accelerated time basis, to permit product manufacturers to gain information as to how their products will stand up to weathering conditions over the months or years.

Typically, an accelerated weathering test apparatus may use air which circulates through the system to control the temperature of samples being tested, so that they are not underheated or overheated by heater or radiation source which may be present, typically a high-intensity plasma lamp such as a xenon lamp. It is desirable for the samples being tested to be exposed to precisely predetermined conditions, to permit more accurate comparison between various testing runs and so that the weathering conditions provided by the test apparatus can be accurately predetermined and thus recreated when desired for comparison of various samples over the years.

In known accelerated weathering test apparatus, a rotatable rack for carrying the samples to be tested surrounds a light source, often a xenon lamp, which emits irradiation having a substantial ultraviolet component. The rack is rotated typically about one revolution per minute, to avoid any systematic differences of positioning of the samples in the system. Also, the typical level of irradiation imposed on the samples is approximately one SUN, which is defined in The Society of Automotive Engineers J-1885 weathering testing method to be 0.55 watt per square meter at 340 nanometers ultraviolet radiation.

Other known accelerated weathering test apparatus further accelerate the aging of materials by exposing such materials to an irradiance level that is higher than one SUN, for example two SUNs (or about 1.1 watts per square meter in accordance with the previous definition). It has been noted that at such higher light intensities, the irregularity of light irradiance around the rack at the area of the samples becomes larger, contributing to sample temperature variations. As a result, the samples may be affected in their testing program by these variables.

Other known accelerated weathering test apparatus monitor and control irradiance of the light source only at three discrete points of the light source SPD. Namely, prior art test apparatus measure light source irradiance only at 340 nanometers ("nm"), 420 nm and 300–400 nm. Measurements are made by a fixed band-pass optical filter and associated closed loop feedback electronics. Standard test methods specify one of the three control points and are not user selectable. These known test monitoring and controlling methods are particularly disadvantageous for several reasons. For example, test specimen materials currently under development are sensitive to, age or degrade as a result of exposure to irradiance from the light source at specific wavelengths other than the set standard. In current instruments it is not possible to control the wavelength of maximum or critical sensitivity for specific materials. Further, the SPD of the light source changes as the light source and inner and outer filters age over time. Again, with a static irradiance control wavelength the optimum accelerated weathering cannot be achieved. As a result, the reliability of the test specimens is affected in their respective testing programs by these variables.

Calibration of known accelerated weathering test apparatus is also cumbersome, time consuming and introduces considerable margin for error into the test results for a client accelerated weathering test apparatus. Prior art calibration schemes are directed to the steps of: calibrating a spectroradiometer from a 1000 watt Tungsten calibration standard; measuring a standard factory light source with the spectroradiometer and assigning a calibration value; calibrating a factory accelerated weathering test apparatus radiometer by operation with the standard factory light source and adjusting radiometer gain in accordance with the calibration value; operating factory accelerated weathering test apparatus with a client standard light source and assigning calibration values based on radiometer readings; and operating a client accelerated weathering test apparatus with the client standard light source and adjusting radiometer gain of client test apparatus to match calibration values. As a result, the possibilities for uncertainties produced by known prior art apparatus is sizeable and vast. Even if the factory executes each of its steps flawlessly, there are still opportunities for the client to make errors. Accordingly, the test specimens are affected in their respective testing program by these variables.

One known weathering apparatus includes a radiation measuring device. A portion of radiation used for testing is guided to the measuring device. The guided radiation is spectrally dispersed so that intensity and/or dosage may be measured by selected diodes at discrete points on the SPD. The radiation detector consists of an array of photodiodes assigned to monitor preselected discrete wave lengths.

Another prior art apparatus for exposing photographic film includes a source of illumination operated at a constant correlated color temperature and intensity. A spectroradiometer takes in light images of the spectrum from 380 nm to 740 nm onto a linear array of thirty-two photodiodes. As a result, the spectral radio meter provides thirty-two signals indicative of the intensity of light in each of the thirty-two uniform which bands together extending from 380 nm to 740 nm. The value of the color temperatures and illuminance for the thirty-two wavelengths nominally at the middle of each of the thirty-two bands are derived from the thirty-two signals from the sensors. From these values, the luminosity of radiant power in color temperature can be derived. The spectroradiometer generates signals indicative of the illuminance and the correlated color temperature, which are transmitted to an automatic control which tests the signals to determine if they are within tolerance. The automatic control and a stepping motor are responsive to signals from the spectroradiometer for adjusting the intensity of a light emitted by the generator. In order to keep color temperature and radiation constant, the distance between the light source and a spherical mirror is altered to adjust the intensity.

Yet another prior art weathering instrument includes a light intensity monitoring and adjusting device including a light guide made of optical fiber, a light receiving section and an adjusting section in a recording instrument. The light guide is configured as a flexible tube containing a bundle of optical fibers which is tri-sected. One end of the light guide is directed toward the lamp and the other, tri-sected, end is connected to the light receiving section. A lens in the light receiving section for each part of the bundle of fibers directs the light to respective light receiving elements, such as photoelectric tubes, through respective filters. The three light receiving elements measure the composition of light at the three fixed, discrete points. One sensor is used to control the intensity of the light and the other two sensors are used to compare what set points to judge the quality of the spectrum.

Still another prior art test apparatus describes a methodology for calibration of a radiometric device with radiation at various intensity levels and spectral distributions. The calibration system includes a light source which emits a beam of light in the direction of a radiometric device for calibrating and/or testing a device. A portion of the light beam is intercepted by the device and another portion of the light beam is intercepted by a detector which is a photodiode. The detector is operated with spectral filtering to view one or more specific spectral bands of interest in the radiation outputted by the light source. The detector provides an output current, via a switch, to a control unit for operating an intensity controller to energize the light source. The current of a single photodetector is asserted to be an accurate predictor of the light intensity within the filtered band for characterizing a linear relationship between photodetector current and intensity.

Therefore, there exists a need in the art for an accelerated weathering test apparatus which overcomes the disadvantages of the prior art, namely: monitoring and controlling a test apparatus with respect to fixed, discrete portions of a light source SPD, inability to calibrate, monitor and control the test apparatus based on the full SPD of a light source, inability to calibrate, monitor and control a test apparatus light source with respect to a user-selectable discrete wavelength, i.e. wavelengths or wavelength range inability to test material sensitivity to different parts of the full SPD, inability to calibrate a test apparatus over a full SPD for a given light source with respect to accepted professional certified standards and inability to monitor changes to the full SPD of a given light source as such light source or associated filters degrade with time.

By the present invention, improvements are provided which increase the accuracy of the calibration, monitoring and control of the test apparatus of this invention. In that the test apparatus can be used to provide accurately predetermined conditions which are substantially predictable and invariant throughout a run and from run to run.

THE BRIEF DESCRIPTION OF THE DRAWINGS

The invention may be best understood by reference to the following description taken in conjunction with the accompanying drawings, in the several figures of which life reference numerals identify like elements.

DETAILED DESCRIPTION OF A PREFERRED EMBODIMENT OF THE INVENTION

Briefly, in one embodiment of the present invention, a method for calibrating an irradiance level control in a client accelerated weathering test apparatus includes the following steps: installing a calibration light source in a factory accelerated weathering test apparatus; operating the factory accelerated weathering test apparatus at a fixed power level as determined by a first calibrated device; collecting a first full SPD of the calibration light source; generating a first group of measurements from the first full SPD; storing the first group of measurements as a first data set; installing the calibration light source in a client accelerated weathering test apparatus; operating the client accelerated weathering test apparatus at the fixed power level as determined by the second calibrated device; collecting a second full SPD for the calibration light source; generating a second group of measurements from the second full SPD; storing the second group of measurements as a second data set; filtering the first and second data sets; aligning the first and second filtered data sets; and determining a system response factor of the client accelerated weathering test apparatus in order to calibrate the irradiance level control of the client accelerated weathering test apparatus.

In another embodiment of the present invention, a method of exposing test specimens in a client accelerated weathering test apparatus to an accurate preselected level of irradiance includes the following steps: determining a power level for generating a preselected level of irradiance from a light source based upon a type of light source filter assembly, a first data set for a calibrated light source and a desired irradiance level set point at a control wavelength from the light source; determining a measured irradiance level from the light source based upon a second data set for the light source adjusted by a system response factor; comparing the power level against the measured irradiance level at the control wavelength; generating a light source power control signal; and repeating the above steps at preselected intervals for a desired period of time.

And yet another embodiment of the present invention is directed to an accelerated weathering test apparatus includes a test chamber. A test specimen mount for supporting test specimens is disposed in the test chamber. A light source is also disposed within the test chamber for generator irradiance. A controller generates a light source power control signal based upon the plurality of inputs. A power source is responsive to the light source power control signal for outputting power to the light source. A spectroradiometer collects a full SPD of the light source then generates a data set representative of the full SPD in order to output the data set to the controller as one of the plurality of inputs.

Figure 1:
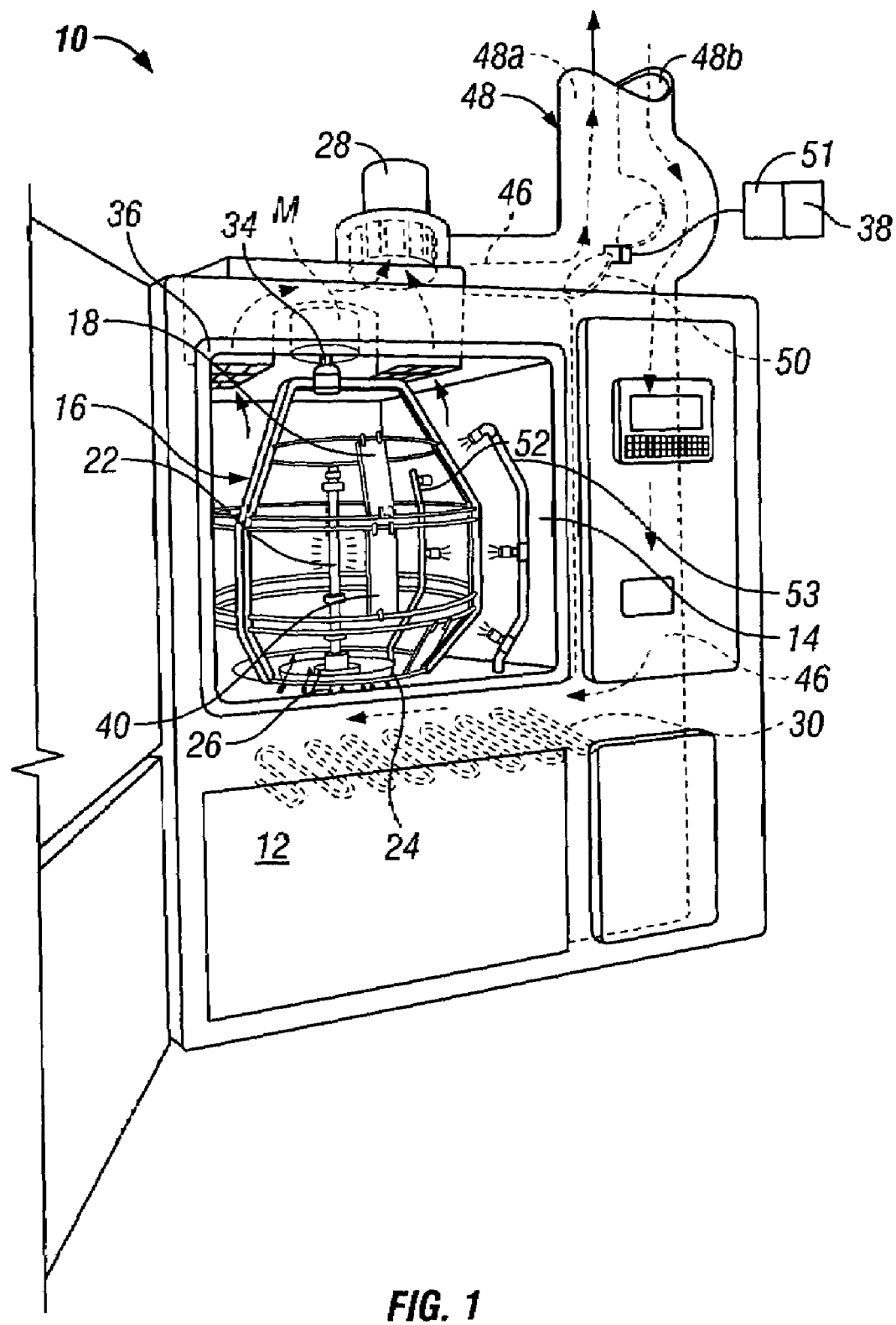
FIG. 1 is a perspective view of a prior art accelerated weathering test apparatus.

Referring to FIG. 1, a weathering testing device 10 is shown, which comprises a housing 12 defining an upper chamber 14 in which a rack 16 resides, comprising a roughly spherical array of stainless steel struts, to which test specimens 18 may be attached in a manner substantially equidistant from a central light source 22, which may be a xenon, fluorescent, metal halide, mercury or tungsten lamp. This arrangement is similar to that disclosed in U.S. Pat. Nos. 5,503,032 and 5,854,433 each of which is fully incorporated herein by reference.

At the bottom of upper chamber 14 a circular arrangement of apertures 26 are provided, plus a conical baffle 24, to assist in directing air passing through apertures 26 along test samples 18 carried on the rack.

A conventional resistance-type heater element 30 may be positioned under apertures 26 and the partition that carries them, for helping to control the temperature of the air surrounding the specimens 18. The fitting of the light source 22 may be in accordance with U.S. Pat. No. 5,226,318, which is fully incorporated herein by reference, including both electrical and water flow conduits for providing the same to the light source 22.

Rack 16 is carried by a first support member or shaft 34 which extends through the top wall 36 of the upper chamber 14. Thus, the connections of various electronic devices carried on rack 16 may pass with shaft 34 through top wall 36 to a microprocessor 38 that is carried in the weathering testing system above top wall 36, in a manner that is safely spaced from both the flowing water and the high electric currents and voltages used with respect to the light source 22.

A motor M is positioned above top wall 36, which rotates shaft 34 and rack 16. Test rack 16 may carry a black panel temperature sensor 40, which is a sensor particularly adapted to sense the temperature directly imparted by the radiation from the light source. A dry bulb sensor may also be provided at a position more remote from light source 22 to monitor air temperature. Also, a direct percentage relative humidity sensor may be provided. Each of these can provide signal data to microprocessor 38.

The top wall also defines wall apertures which represent the inlet of a circulatory plenum 46 that circulates air, driven by blower 28, from top to the bottom of chamber 14 and through apertures 26, as propelled by blower 28.

Within plenum 46 is a variably openable cooling air supply vent 48, having a movable damper 50, and comprising air inlet 48b and air outlet 48a. The position of the damper 50 can be controlled by a control member 51 which is, in turn, controlled by the microprocessor 38 in a conventional manner.

Rack water spray or atomizer unit 52 is also provided in upper chamber 14, along with a specimen water sprayer atomizer unit 53, provided for added specific spraying of the specimens when that is desired.

Further details with respect to weathering test machine 10 may be as disclosed in the previously cited U.S. Pat. Nos. 5,503,032 and 5,854,433.

Figure 2A:
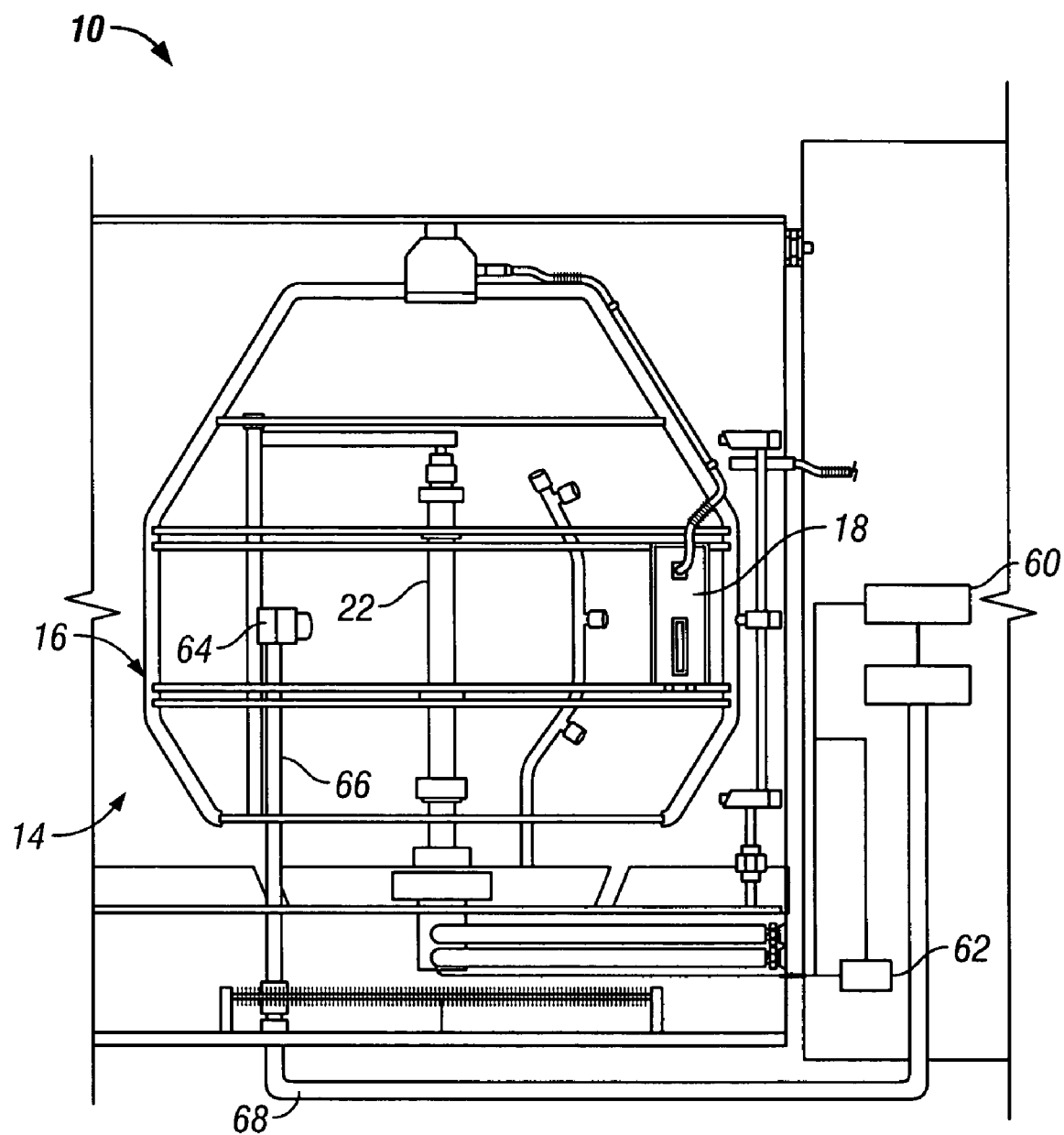
FIG. 2A is an elevation view of an accelerated weathering test apparatus in accordance with one embodiment of the present invention.
Figure 2B:
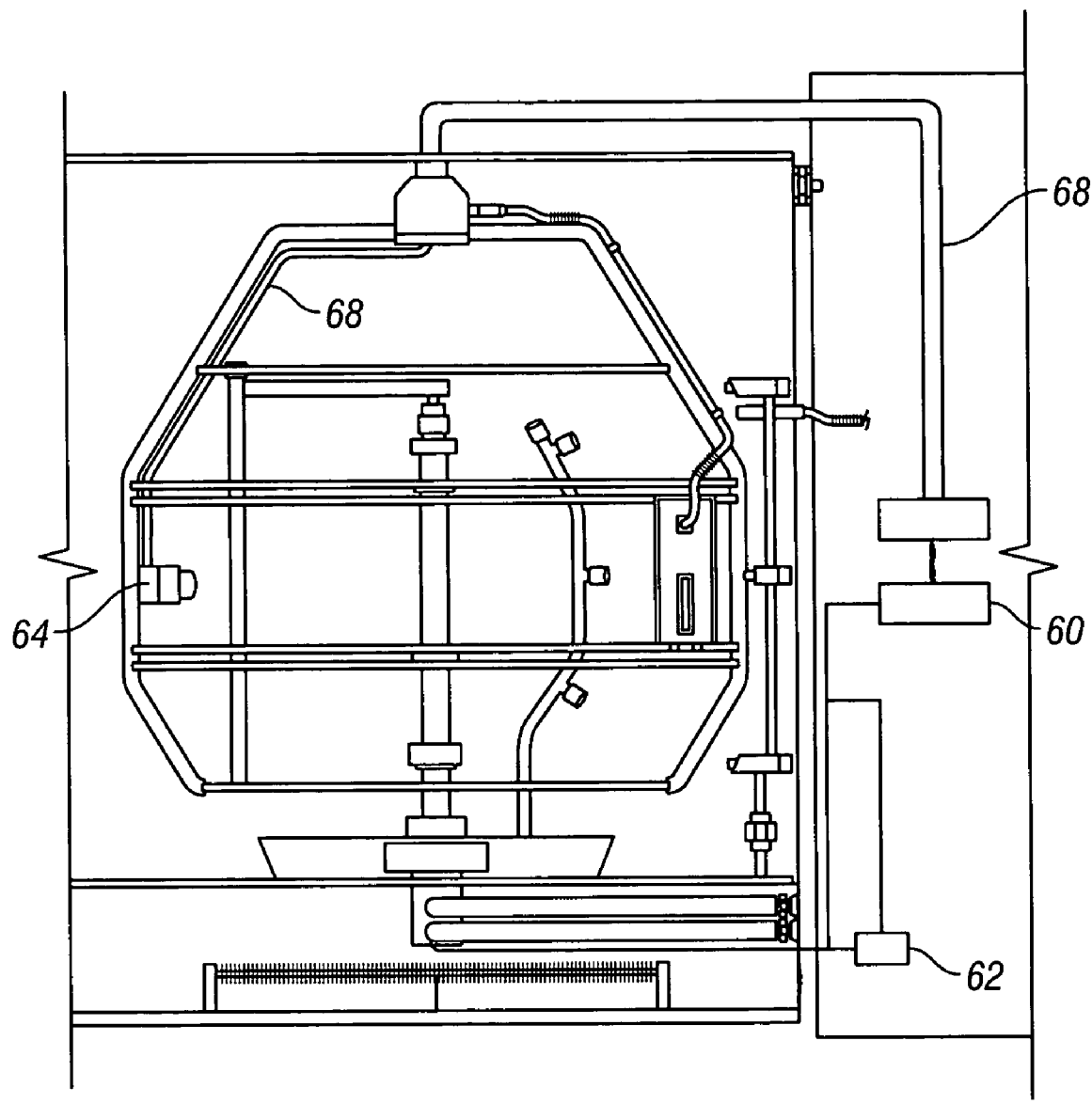
FIG. 2B is an elevation view of an accelerated weathering test apparatus in accordance with another embodiment of the present invention.

Referring to FIGS. 2A and 2B, an elevation view of an accelerated weathering test apparatus 10 in accordance with embodiments of the present invention are illustrated. It will be recognized by those of skill in the art that the structural and functional aspects of the embodiments of the present invention are as set forth above with respect to such aspects described and explained in connection with FIG. 1, except for the further details set forth below. Accordingly, further description of this embodiment will be directed to only those structural and functional aspects of the present embodiment and such aspects of the embodiment described in FIG. 1 necessary to support and enable the description of the embodiments in FIGS. 2A and 2B. It is within the teachings of the present invention that the structural and functional aspects of the apparatus described with respect to FIG. 1 and the references incorporated herein shall apply and enable any of the embodiments of the present invention.

The accelerated weathering test apparatus 10 of these embodiments include an upper or test chamber 14, a rack or test specimen mount 16 for supporting test specimens 18 in the test chamber 14. A light source 22 is disposed within the test chamber 14 for generating irradiance in the test chamber 14. A controller 60 generates a light source power control signal based upon a plurality of inputs, as will be discussed below. A power source 62 responsive to the light source power control signal for outputting power to the light source 22. An input device 64 is disposed within the test chamber 14 for direct interface with irradiance from the light source 22 in order to facilitate and enable monitoring of the full SPD of the light source 22. A data set representative of the full SPD is generated and outputted to the controller 60 as one of the plurality of inputs.

The controller 60 determines a power level for generating a preselected level of irradiance from the light source 22 based upon a plurality of inputs. Preferably, the plurality of inputs include at least the following: a type of light source filter assembly; a calibrated light source data set (as described below); and a desired irradiance level set point for a control wavelength from the light source 22. It is within the teachings of the present invention that additional inputs to the controller 60 may be desired and used to facilitate and enable more precise control over the power level.

The controller further determines a measured irradiance level from the light source 22 based upon the data set for the light source 22 adjusted by a system response factor, each described in more detail below. It will be recognized by those of skill in the art that the term "data set" as used in connection with the embodiment described with respect to FIGS. 2A and 2B is equivalent to the term "second data set" as used hereafter and may be used interchangeably therewith. The controller 60 compares the power level and the measured irradiance level, generates a light source power control signal which is outputted to the power source 62 and repeats the above steps at preselected intervals for a desired period of time. Thereby, precise and accurate operation of the accelerated weathering test apparatus that overcomes the disadvantages of the prior art may be accomplished.

Preferably, the controller 60 includes a processing unit and memory that stores programming instructions that, when used by the processing unit, causes the controller to function to: determine a power level for generating a preselected level of irradiance from a light source based upon a type of light source filter assembly, a calibrated light source data set and a desired irradiance level set point at a control wavelength from the light source; determine a measured irradiance level from the light source based upon the data set for the light source adjusted by a system response factor; compare the power level and the measured irradiance level; generate a light source power control signal; and repeat the above steps at preselected intervals for a desired period of time.

The processor in this invention may be, but not limited to, a single processor, plurality of processors, a DSP, a microprocessor, ASIC, state machine, or any other implementation capable of processing and executing software. The term processor should not be construed to refer exclusively to hardware capable of executing software, and may implicitly include DSP hardware, ROM for storing software, RAM, and any other volatile or non-volatile storage medium.

The memory in this invention may be, but not limited to, a single memory, a plurality of memory locations, shared memory, CD, DVD, ROM, RAM, EEPROM, optical storage, microcode or any other non-volatile storage capable of storing digital data for use by the processor.

The power source 62 is the same as used in connection with the embodiment described in FIG. 1. However, operation in connection with the controller 60 now enables the power source 62 to be adjusted such that a reliably consistent irradiance level is provided during any test.

The input device may be a spectroradiometer, a receiving optic device or any other suitable input device that is disposed within the test chamber 14 for direct interface with irradiance from the light source 22 and operatively communicates with a spectroradiometer. In FIG. 2A, the input device 64 is disposed on a stand 66 within the circumference of the test specimen mount 16. In FIG. 2B, the input device 64 is mounted on the test specimen mount 16 as would a test specimen in a test specimen plane defined by such test specimen supported by the test specimen mount or rack.

In the event the input device 64 is the receiving optic device or other suitable device other than a spectroradiometer disposed within the test chamber 14 for direct interface with irradiance from the light source 22 as shown in either of FIGS. 2A or 2B, a lightwave guide facilitates and is useful for channeling the light from the light source to the spectroradiometer which is disposed remote from the test chamber 14 or within and not exposed to direct irradiance.

Generally the spectroradiometer may be, but not limited to, any suitable device having a monochromator and a photosensitive device or a diode array. Preferably, the spectroradiometer is a linear charged coupled device that can be calibrated to National Institute of Standards and Testing ("NIST") standards. For example, one suitable spectroradiometer useful in connection with the present invention may be model number OL 754-C from Optronic Laboratories of Orlando, Fla. Other suitable spectroradiometers which facilitate or enable the functional aspects of the present invention may also be used.

As described above, the light source 22 may be a lamp selected from the group consisting of xenon, fluorescent, metal halide, mercury and tungsten lamps. It will be recognized by those of skill in the art that other suitable light sources known or later discovered may be used to provide the desired results.

FIGS. 3A, 3B, 3C, 3D, 3E and 4 illustrate flow charts directed to various steps for calibration of an irradiance level control in a client accelerated weathering test apparatus in accordance with the various embodiments of the present invention. Initially, the factory accelerating weathering test apparatus must be calibrated. More particularly, the spectroradiometer used in connection with the factory accelerated weathering test apparatus must be calibrated in accordance with known standards in order to provide the precision and accuracy in the later steps of the calibration procedure of the present invention. A known standard test method for calibration of a spectroradiometer using a standard source of irradiance is set forth in the American Society for Testing and Materials Publication G138, "*Standard Test Method For Calibration of a Spectroradiometer Using a Standard Source of Irradiance,* March 1996; which is fully incorporated herein by reference. A standard source of irradiance or calibration light source may be a lamp selected from the group consisting of xenon, fluorescent, metal halide, mercury and tungsten lamps. It will be recognized by those of skill in the art that other suitable calibration light sources known or later discovered may be used to provide the desired results.

Figure 3A:
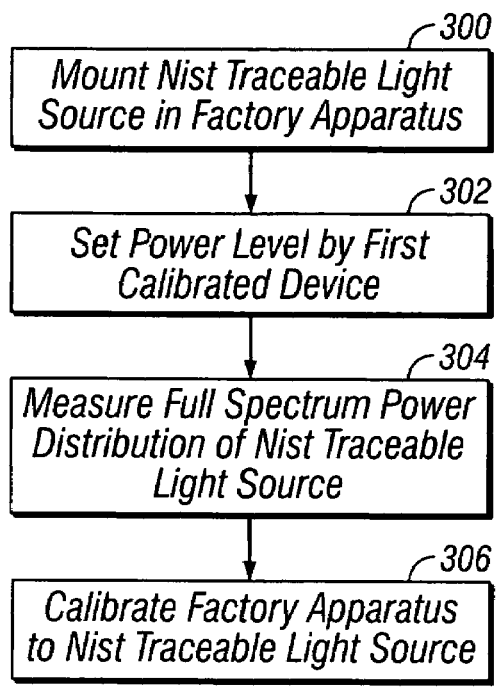
FIG. 3A is a flow chart directed to the steps for calibration of an accelerated weathering test apparatus in accordance with one embodiment of the present invention.

Briefly, the steps illustrated in FIG. 3A are directed to this initial setup of the factory accelerated weathering test apparatus. In step 300, a NIST-traceable light source is mounted in the factory accelerated weathering test apparatus in accordance with known standards. In step 302, a first calibrated device is used to set a fixed power level for the NIST-traceable light source. For example, the first calibrated device may be a wattmeter or other suitable power level control device. Preferably, the first calibrated device and other calibrated devices mentioned herein are configured as NIST-traceable wattmeters. In step 304, the factory accelerated weathering test apparatus is operated in accordance with the above steps such that the spectroradiometer operatively coupled to the factory accelerated weathering test apparatus measures a full SPD of the NIST-traceable light source. As a result, in step 306, the factory accelerated weathering test apparatus is calibrated to the NIST-traceable light source.

Figure 3B:
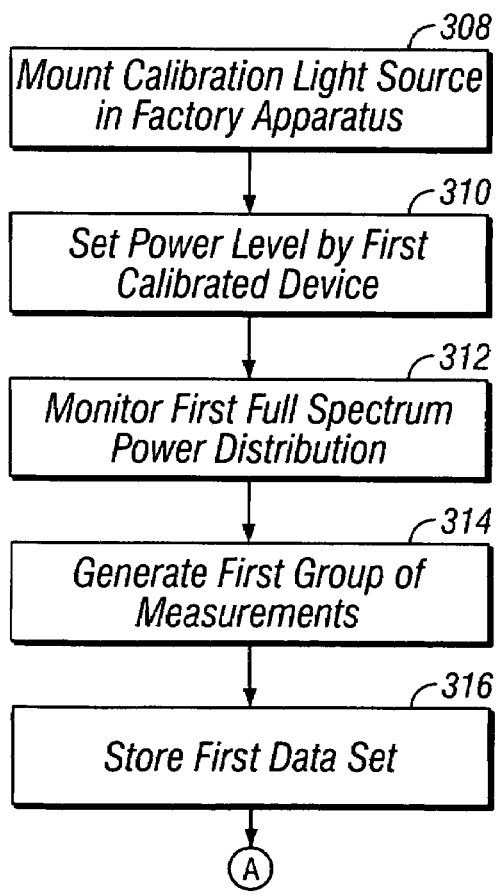
FIG. 3B is a flow chart directed to additional steps for calibration of the accelerated weathering test apparatus of FIG. 3A.

FIG. 3B is a flow chart directed to the next additional steps for calibrating the irradiance level control in the client accelerated weathering test apparatus. In step 308, a calibration light source is mounted in the factory accelerated weathering test apparatus. In step 310, the first calibrated device is used to set the fixed power level for operating the factory accelerated weathering test apparatus. In step 312, during operation of the factory accelerated weathering test apparatus, the NIST-traceable calibrated spectroradiometer collects a first full SPD of the calibration light source. In step 314, the NIST-traceable spectroradiometer generates a first group of measurements from the first full SPD. In step 316, the first group of measurements are stored as a first data set.

Figure 5:
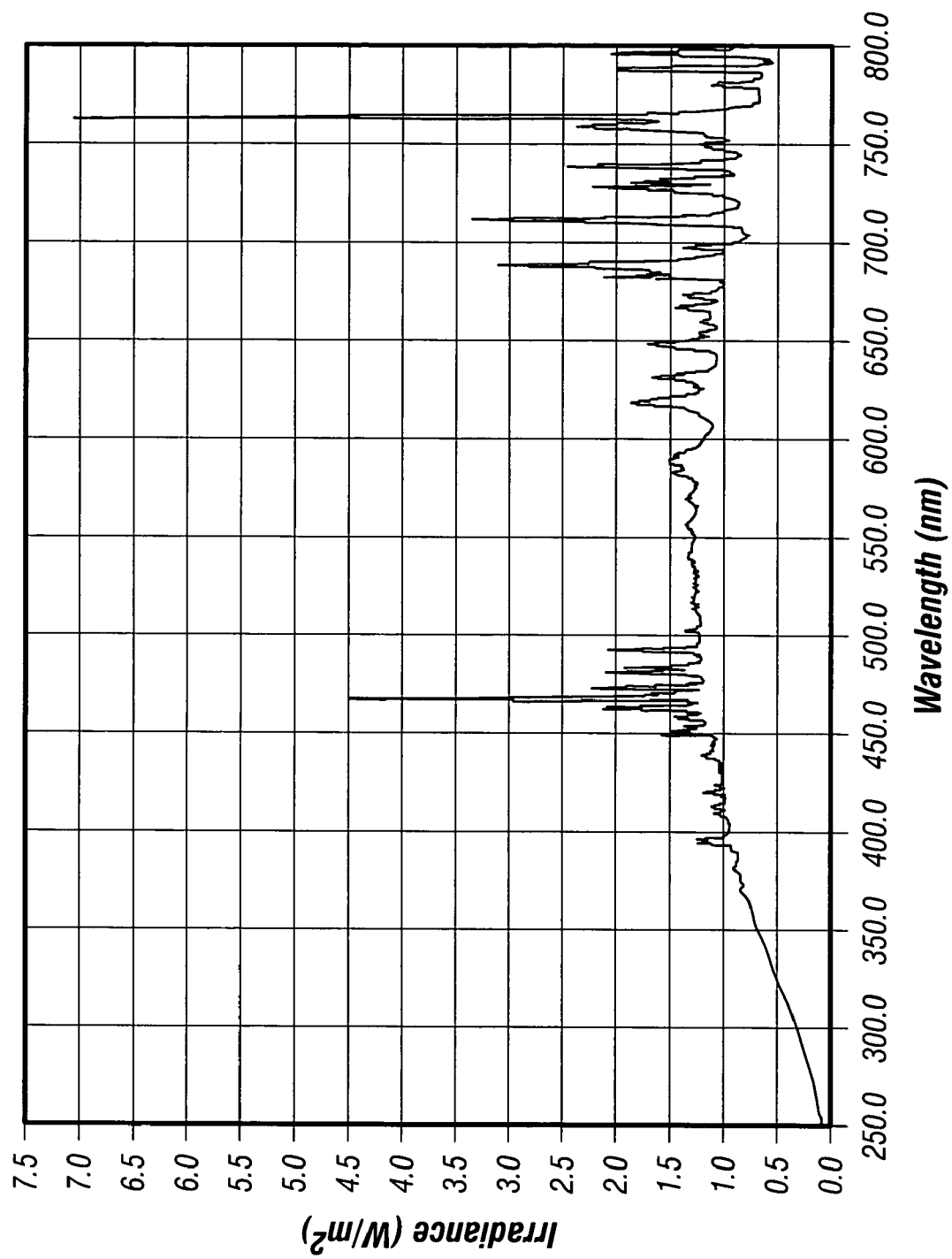
FIG. 5 is a graphical representation of a portion of the SPD for a calibration light source monitored by a traceable spectroradiometer.

Further with respect to the first and/or groups of measurements, the equally spaced intervals are approximately 1 nanometer, less than 1 nanometer or greater than 1 nanometer. FIG. 5 is a graphical representation of a portion of the first full SPD for the calibration light source as collected by the NIST-traceable spectroradiometer in accordance with one embodiment of the present invention. The first data set is useful to facilitate or enable calibration of the client accelerated weathering test apparatus and the operation thereof as will be described below. It will be recognized by those of skill in the art that the units along the X-axis are wavelengths as measured in nanometers and the units along the Y-axis are irradiance as measured in watts per square meter. Each measurement of the first group of measurements is expressed as a first irradiance amplitude for each of a plurality of discreet wavelengths in equally spaced intervals over the first full SPD.

The first data set is preferably captured in a data store or memory which may be, but is not limited to, a single memory, plurality of memory locations, shared memory, CD, DVD, ROM, RAM, EPROM, optical storage, macrocode or any other non-volatile storage capable of storing digital data for use by a processor. More preferably, the first data set is captured in a portable data store or memory which can be transmitted, forwarded or distributed with the calibration light source for use in connection with a client accelerated weathering test apparatus.

Figure 3C:
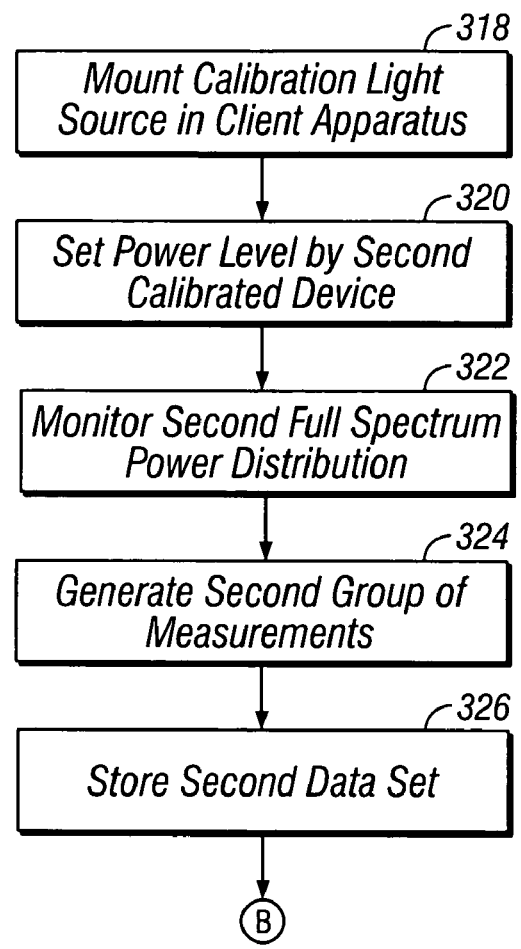
FIG. 3C is a flow chart directed to additional calibration steps for the accelerated weathering test apparatus of FIG. 3A.
Figure 6:
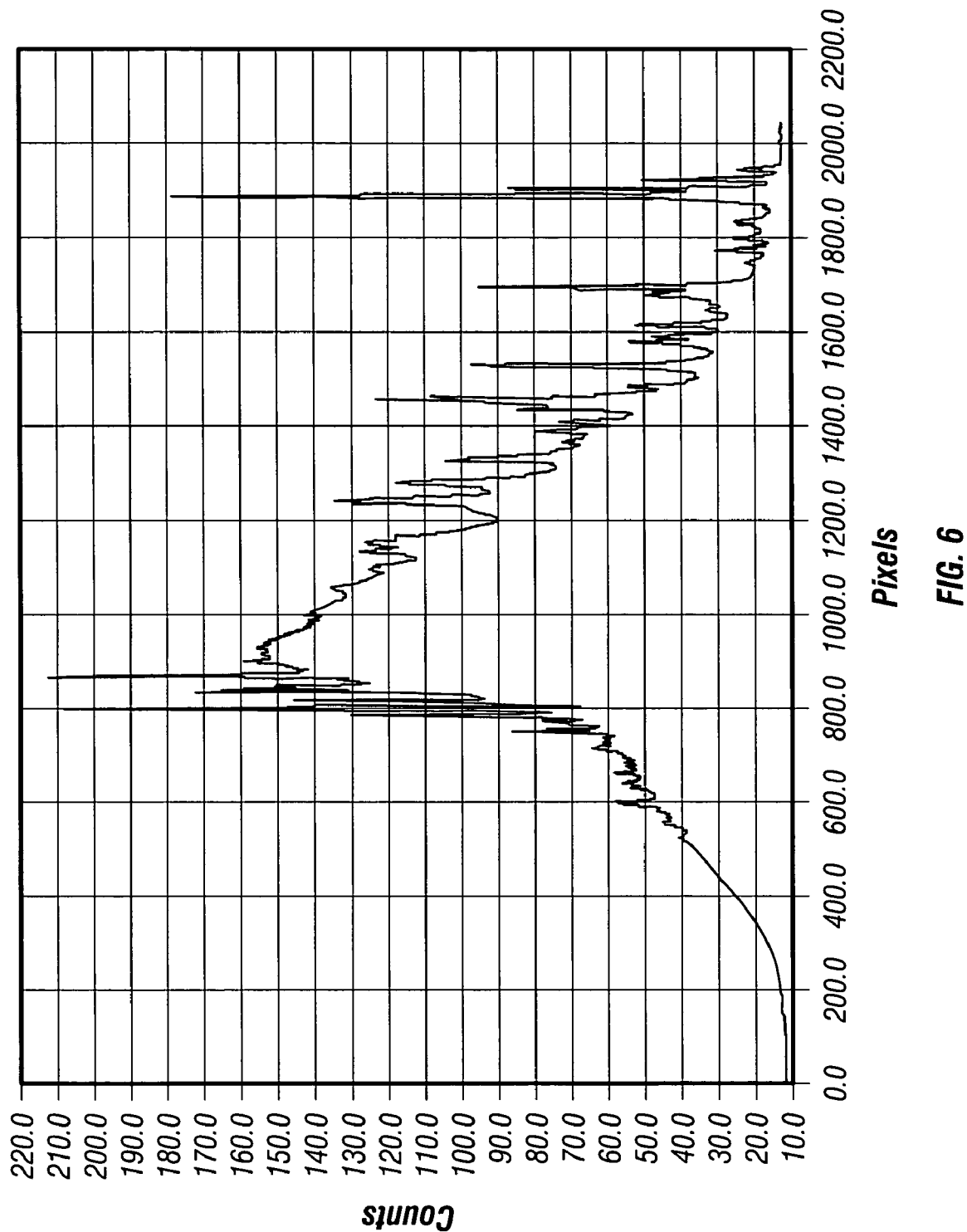
FIG. 6 is a graphical representation of a second group of measurements from a second full SPD for the calibration light source operated in a client accelerated weathering test apparatus.

FIG. 3C is a flow chart directed to additional calibration steps for calibrating the irradiance level control in the client accelerated weathering test apparatus. In step 318, the calibration light source is installed in the client accelerated weathering test apparatus. In step 320, a second calibrated device is used to set a fixed power level to operate the client accelerated weathering test apparatus. As discussed above, the second calibrated device may be any such suitable device and preferably a NIST-traceable wattmeter. In step 322, a spectroradiometer operatively coupled to the client accelerated weathering test apparatus collects a second full SPD for the calibration light source. In step 324, a second group of measurements from the second full SPD is generated. In step 326, the second group of measurements is stored as a second data set. FIG. 6 is a graphical representation of the second group of measurements from the second full SPD for the calibration light source operated in the client accelerated weathering test apparatus in accordance with one embodiment of the present invention. It will be recognized by those of skill in the art that the units along the X-axis are pixels (of the linear charge coupled device in this embodiment) and the units along the Y-axis are counts (observed by the pixels). In other words, in this embodiment of the present invention, a linear charge coupled device is used as a spectroradiometer and each sensor element or pixel observes the number of counts which are representative of the intensity of a certain wavelength of the second full SPD. The second data set is preferably stored in a memory or data source as "memory" has been defined and used herein.

Figure 3D:
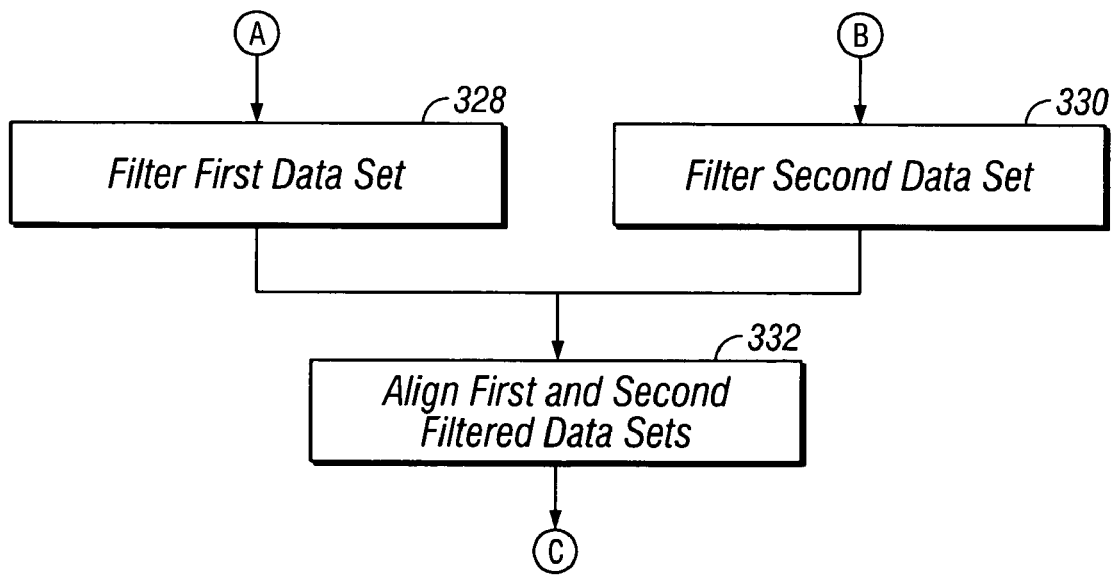
FIG. 3D is a flow chart directed to additional calibration steps for the accelerated weathering test apparatus of FIG. 3A.
Figure 7:
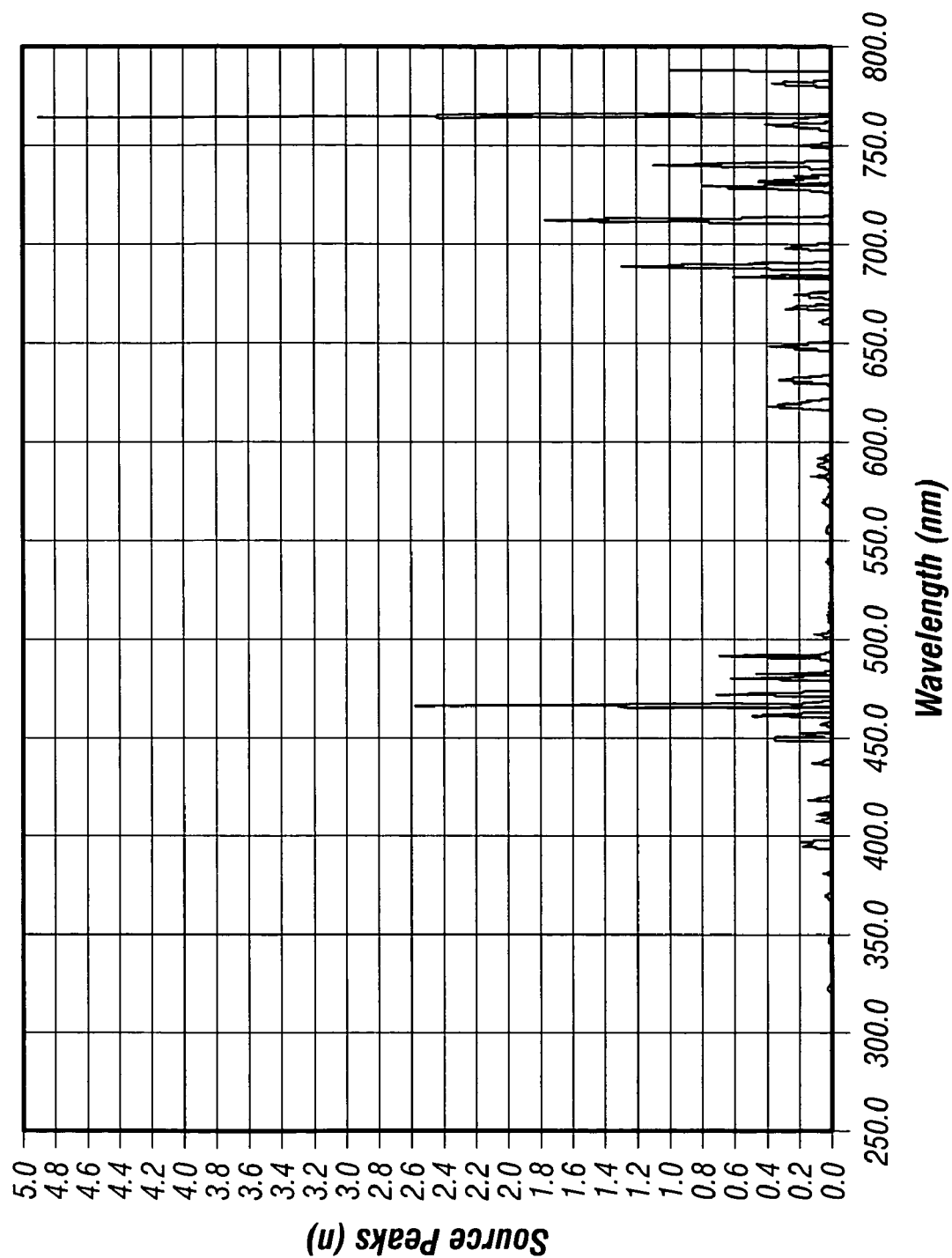
FIG. 7 is a graphical representation of the first full SPD of the calibration light source after filtering.
Figure 8:
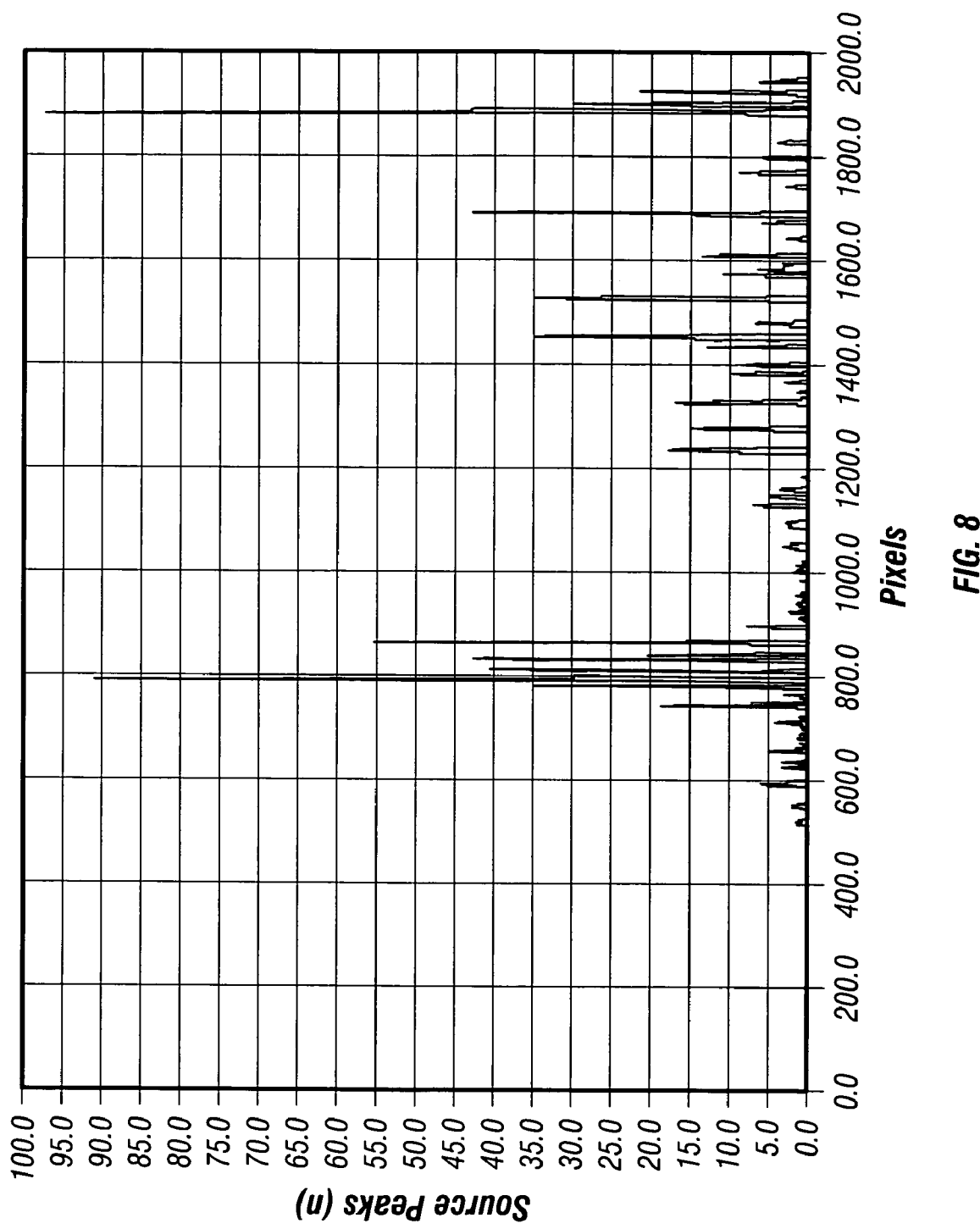
FIG. 8 is a graphical representation of the second full SPD of the calibration light source of FIG. 6 after filtering.

FIG. 3D is a flow chart directed to additional calibration steps for calibrating the irradiance level control in a client accelerated weathering test apparatus. In step 328, the first data set is filtered. FIG. 7 is a graphical representation of the first full SPD of the calibration light source of FIG. 5 or first data set after filtering in accordance with one embodiment of the present invention. In step 330, the second data set is filtered. FIG. 8 is a graphical representation of the second full SPD of the calibration light source of FIG. 6 or second data set after filtering in accordance with one embodiment of the present invention. Generally, each of the filtering steps uses an algorithm to isolate and identify source peaks of the first and second full SPDs. Preferably, the step of filtering uses the algorithm:

$$y_i = x_i - \left[ 1/16 \times \sum_{j=0}^{j=6} (4 - |j-3|) \cdot x_{(i-(j-3))} \right]$$

where y=one of the filtered data sets;
x=the other of the filtered data sets;
i=Index digit, to isolate and identify source peaks of the first and second full SPDs.

The algorithm generally is an indexing equation for mathematical curve smoothing. Preferably, the algorithm subtracts a mathematically smoothed curve from the original curve to isolate and identify source peaks of each of the first and second full SPDs.

Figure 4:
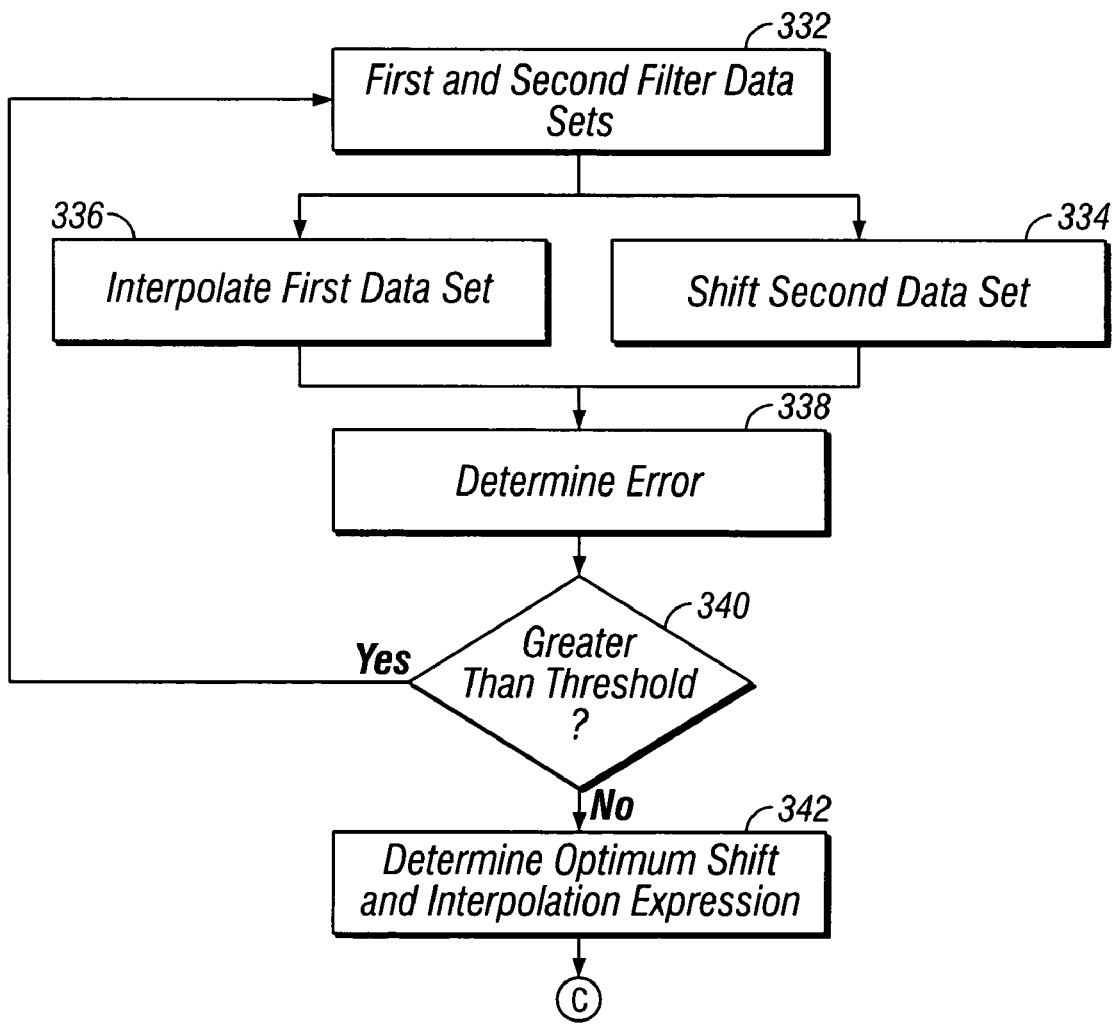
FIG. 4 is a flow chart directed to a step of filtering in FIG. 3D.
Figure 9A:
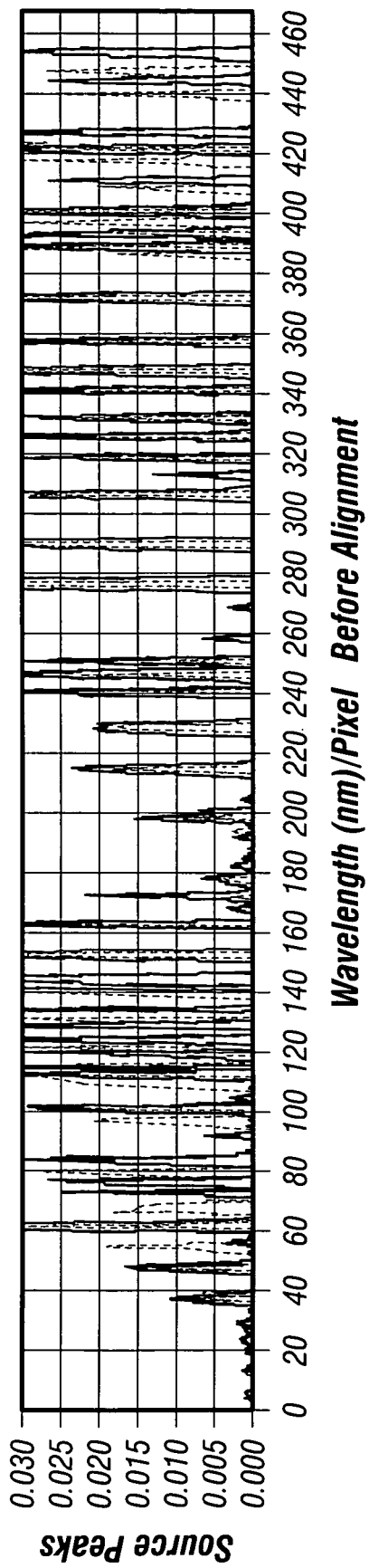
FIG. 9A is a graphical representation of an initial aligning step for the first and second filtered data sets.

In step 332, the first and second filtered data sets are aligned. FIG. 4 is a flow chart directed to the step of aligning discussed in step 332. FIG. 9A is a graphical representation of an initial aligning step for the first and second filtered data sets. It will be reorganized by those of skill in the art that the units along the x-axis are wavelength per pixel and along the y-axis as source peaks. Initially, there is a difference or error delta between the wavelength (first data set) and pixel (second data set) data. In step 334, the second data set is shifted by a pre-selected increment. In step 336, the first data set is interpolated in increments of the derived error delta or offset by a wavelength offset. In step 338, an error between the shifted second data set and the interpolated first data set is determined. In step 340, the error is compared against a pre-selected threshold. In the event the error is greater than the pre-selected threshold, the step of aligning the first and second filtered data sets is repeated in accordance with the above steps. Preferably, the pre-selected threshold is approximately in the range the provides acceptable accuracy. It will be recognized by one of skill in the art that the threshold is dependant on the light source and the spectroradiometer. In step 342, if the error is less than the pre-selected threshold, an expression for an optimum shifted second data set and interpolated first data set is determined and the normalization or alignment of respective data sets.

Figure 9B:
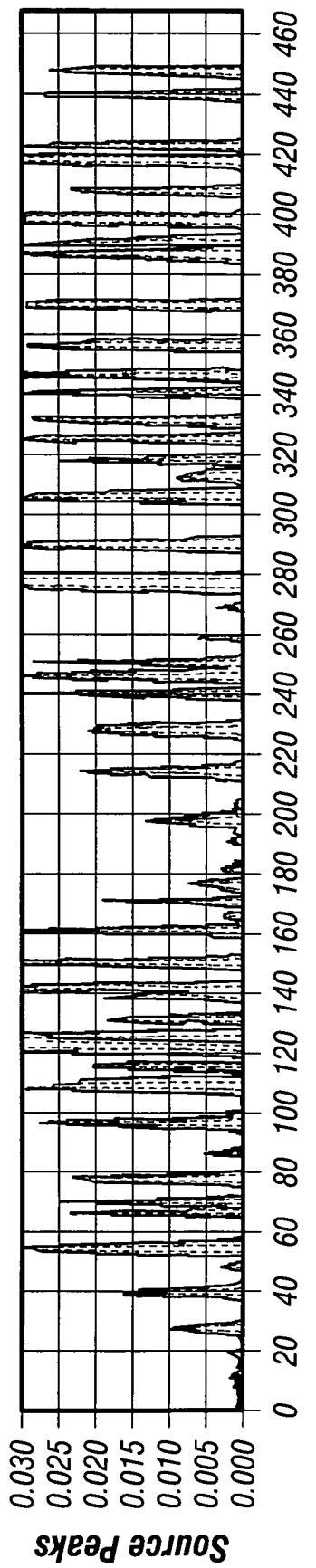
FIG. 9B is a graphical representation of a subsequent step of aligning the first and second filtered data sets.

FIG. 9B is a graphical representation of a subsequent step of aligning the first and second filtered data sets after the error is less than threshold and the optimum shift and interpolation expression has been determined. Again, it will be recognized that the units along the x- and y-axis are the same as FIG. 9a.

Figure 3E:
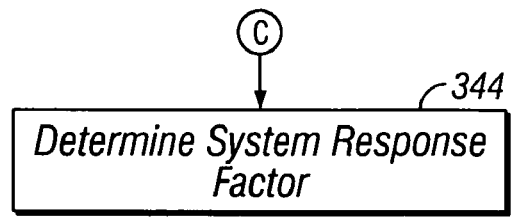
FIG. 3E is a flow chart directed to additional calibration steps for the accelerated weathering test apparatus of FIG. 3A.

FIG. 3E is a flow chart directed to additional calibration steps for calibrating an irradiance level control in a client accelerated weathering test apparatus. In step 344, a system response factor of the client accelerated weathering test apparatus is determined in order to calibrate the irradiance level control of the client accelerated weathering test apparatus. The system response factor is based on the filtered first and second data sets and the optimum shift and interpolation expression. As a result, the system response factor represents a discrete wavelength specific ratio of the output signal to the input stimulus, as described herein. The steps in determining the system response factor includes finding the ratio of the output to the input for each wavelength over a full SPD.

Figure 10:
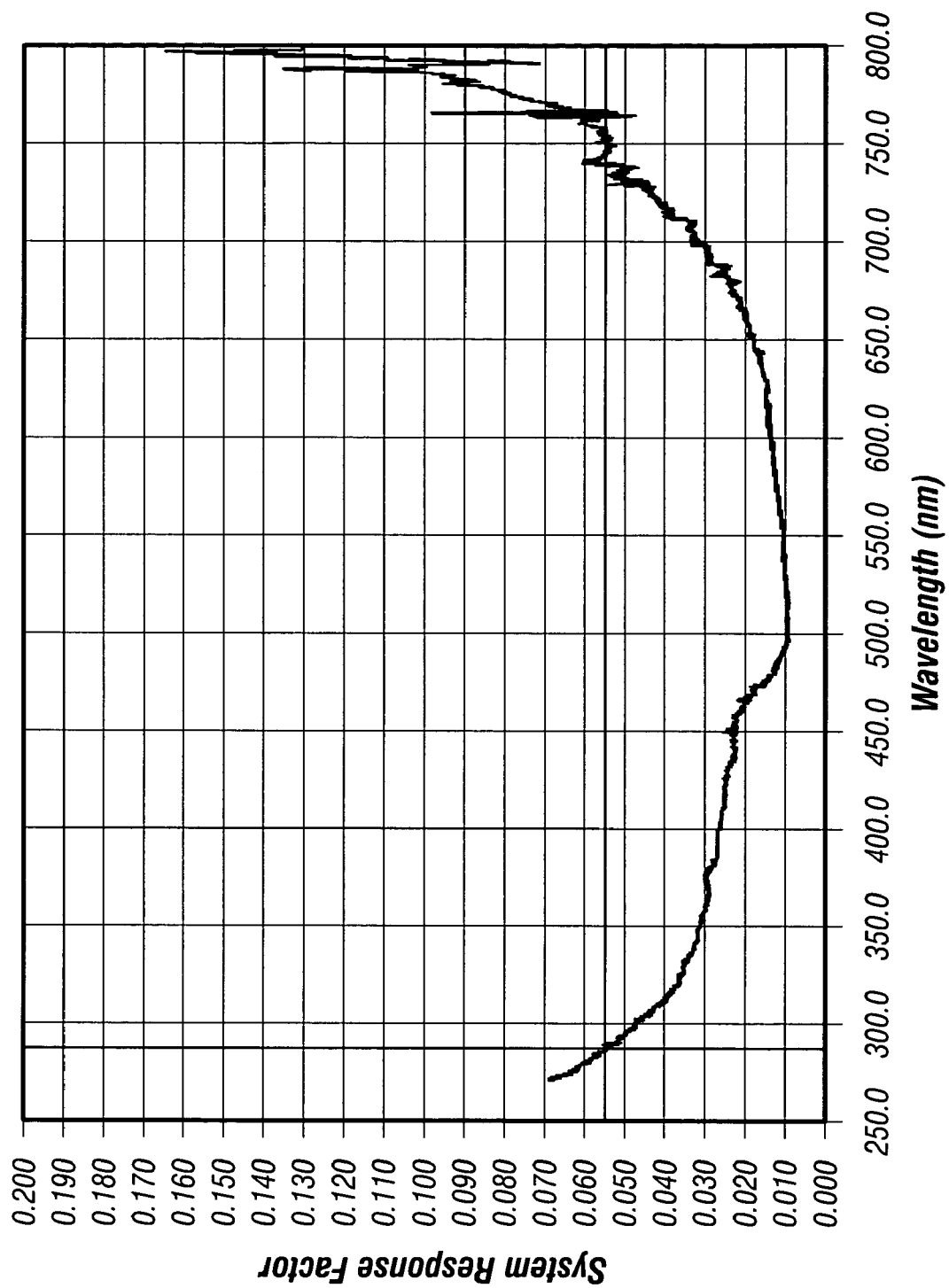
FIG. 10 is a graphical representation of a system response factor of the client accelerated weathering test apparatus.

FIG. 10 is a graphical representation of a system response factor of the client accelerated weathering test apparatus in accordance with one embodiment of the present invention. It will be recognized by those of skill in the art that the system response factor is expressed as a signal output amplitude of each of a plurality of discreet wavelengths of a full SPD with respect to the client accelerated weathering test apparatus. In other words, as will be discussed in more detail below, the system response factor is useful to adjust the irradiance level control for a particular client accelerated weathering text apparatus to a NIST traceable level.

Figure 11:
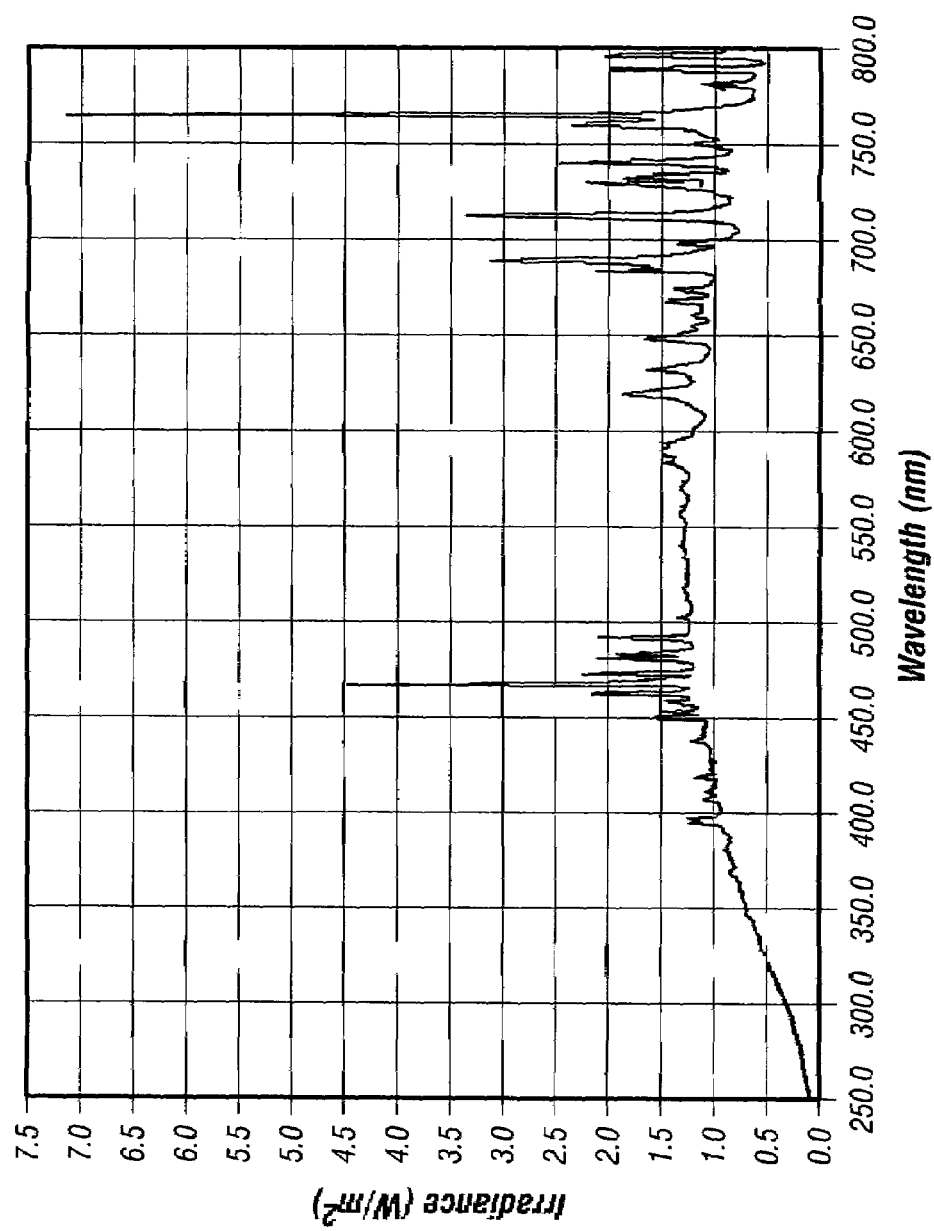
FIG. 11 is a graphical representation of the full SPD of the client accelerated weathering test apparatus after calibration.

FIG. 11 is a graphical representation of a full SPD generated by the client accelerated weathering test apparatus after calibration. It will be recognized by those of skill in the art that the graphical representation of the full SPD of FIG. 11 is substantially identical to the graphical representation of the full SPD of FIG. 5 indicating that the irradiance level control in the client accelerating weathering test apparatus is now calibrated to a NIST-traceable level. As a result, accurate and predictable results may be obtained from the client accelerated weathering test apparatus.

In one embodiment of the present invention, the step of collecting the first full SPD, is facilitated by a NIST-traceable spectroradiometer used in connection with the factory accelerated weathering test apparatus. Such spectroradiometer may include a monochromator and a photosensitive device and may be selected from the group consisting of a linear charged coupled device and a diode array.

It is within the teachings of the present invention that the step of collecting the second full SPD is facilitated by a spectroradiometer used in connection with the client accelerated weathering test apparatus. Such spectroradiometer preferably may include a monochromator and a photosensitive device which may be selected from the group consisting of a linear charged coupled device and a diode array.

Figure 12:
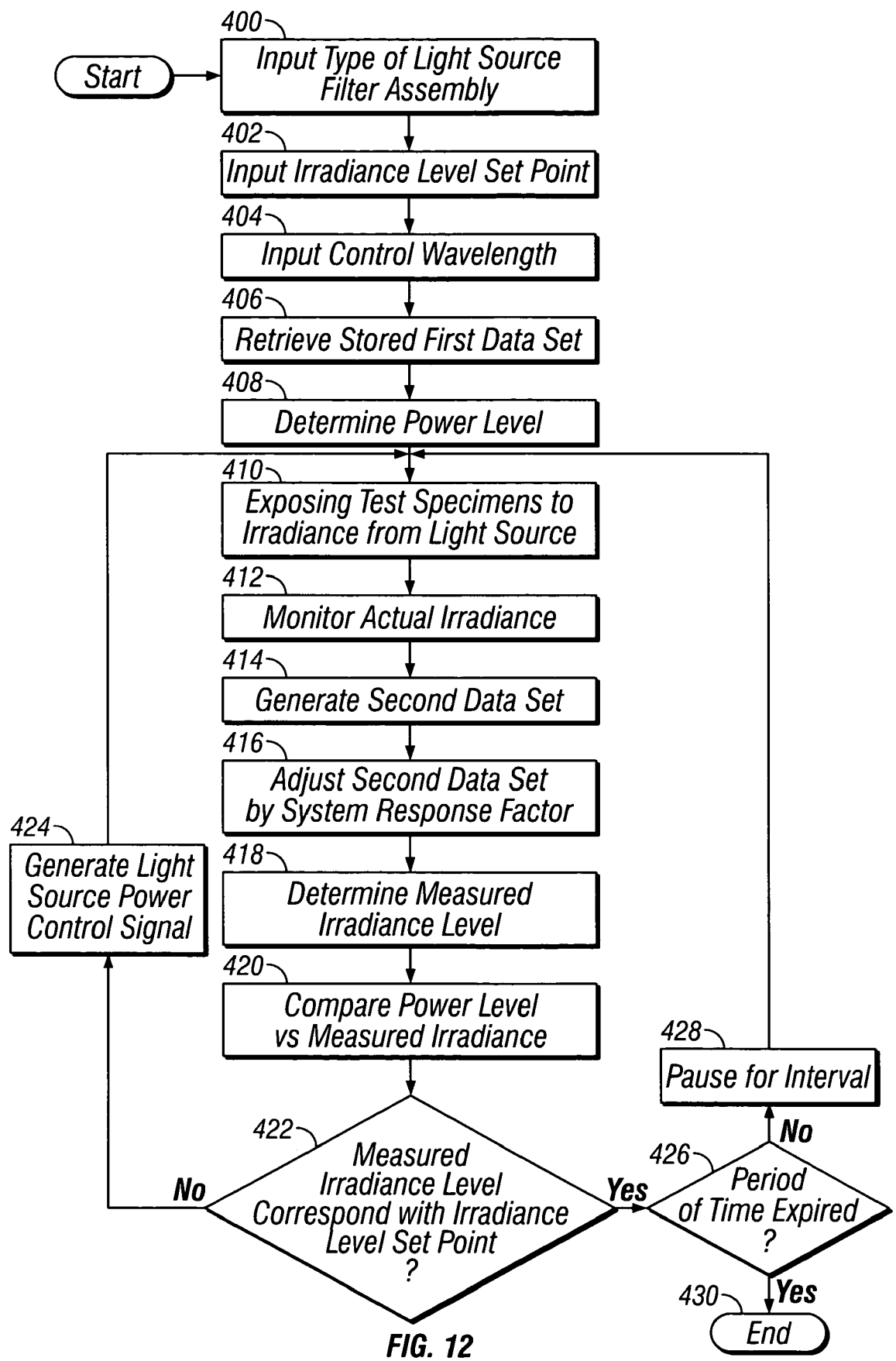
FIG. 12 is a flow chart directed to the steps in accordance with one embodiment of the present invention for operating the calibrated client accelerated weathering test apparatus.

FIG. 12 is a flow chart directed to the steps in accordance with one embodiment of the present invention for operating the calibrated client accelerated weathering test apparatus to expose test specimens therein to an accurate pre-selected level of irradiance. In step 408, a power level for generating a pre-selected level of irradiance from a light source is determined. The process of determining the power level is based on preceding steps 400–406. Namely, a type of light source filter assembly is inputted in step 400, a desired irradiance level set point for a control wavelength from the light source is inputted in steps 402 and 404, and a first data set for a calibrated light source is retrieved from memory in step 406. In step 410, the client accelerated weathering test apparatus is activated in order to begin exposing test specimens to irradiance from the light source.

A measured irradiance level from the light source is observed in step 418 based upon the preceding steps. Namely, the actual irradiance from the light source is collected and conditioned in step 412, a second data set is generated in step 414 and the second data set is adjusted by a system response factor in step 416.

In step 420, the power level and the measured irradiance level at the control wavelength are compared. In the event the measured irradiance level does not correspond with the irradiance level set point, an adjusted light source power control signal is generated in step 424 and the process resets back to step 410. In the event the measured irradiance level corresponds with the irradiance level set point and the desired time period for exposure is not expired in step 426, then the process of this embodiment of the present invention pauses for an interval in step 428 and, after the pause, resets the process to step 410. In the event the desired time period for exposure is expired in step 426, the exposure of the test specimens in the client accelerated weathering test apparatus ends in step 430.

It is within the teachings of the present invention that the control wavelength may be a range of wavelengths or a specified range of wavelengths and that such may be used to determine photometric output. For example, a LUX value may be determined from any full SPD derived in accordance with the present invention applied to a mathematical function known to those of skill in the art. In one embodiment of the present invention, this may be characterized by the raw data weighted with respect to a human eye, i.e. photopic response In one embodiment of the present invention, the first data set includes a first group of measurements from a first full SPD where each measurement of the first group of measurements is expressed as a first irradiance amplitude for each of a plurality of discreet wavelengths in equally spaced intervals over the first full SPD. Preferably, the first group of measurements is enabled by a NIST-traceable spectroradiometer.

Further in one embodiment of the present invention, the second data set includes a second group of measurements from a second full SPD where each measurement of the second group of measurements is expressed as a number of counts for each sensor element. The second group of measurements is enabled by a NIST-traceable spectroradiometer and such spectroradiometer may be a linear charged coupled device or any other suitable device.

Various modifications and changes may be made by those skilled in the art without departing from the true spirit and scope of the invention, as defined by the depending claims. For example, the apparatus may be configured to operate with the advantages described herein with respect to other suitable light sources, calibration light sources and spectroradiometers.

What is claimed is:

1. A method for calibrating an irradiance level control in a client accelerated weathering test apparatus, comprising the steps of:

installing a calibration light source in a factory accelerated weathering test apparatus;

operating the factory accelerated weathering test apparatus at a fixed power level as determined by a first calibrated device;

collecting a first full spectrum power distribution ("SPD") of the calibration light source;

generating a first group of measurements from the first full SPD;

storing the first group of measurements as a first data set;

installing the calibration light source in a client accelerated weathering test apparatus;

operating the client accelerated weathering test apparatus at the fixed power level as determined by a second calibrated device;

collecting a second full SPD for the calibration light source;

generating a second group of measurements from the second full SPD;

storing the second group of measurements as a second data set;

filtering the first and second data sets;

aligning the first and second filtered data sets; and determining a system response factor of the client accelerated weathering test apparatus in order to calibrate the irradiance level control of the client accelerated weathering test apparatus.

2. A method as recited in claim 1, wherein the step of collecting the first full SPD is facilitated by a National Institute of Standards and Testing ("NIST")-traceable spectroradiometer used in connection with the factory accelerated weathering test apparatus.

3. The method as recited in claim 2, wherein the spectroradiometer includes a monochromator and a photo-sensitive device.

4. The method as recited in claim 2, wherein the spectroradiometer is selected from the group consisting of a linear charge coupled device and a diode array.

5. The method as recited in claim 1, wherein the step of collecting the second full SPD is facilitated by a spectroradiometer used in connection with the client accelerated weathering test apparatus.

6. The method as recited in claim 5, wherein the spectroradiometer includes a monochromator and a photo-sensitive device.

7. The method as recited in claim 5, wherein the spectroradiometer is selected from the group consisting of a linear charge coupled device and a diode array.

8. The method as recited in claim 1, wherein each measurement of the first group of measurements is expressed as a first irradiance amplitude for each of a plurality of discrete wavelengths at equally spaced intervals over the first full SPD.

9. The method as recited in claim 8, wherein the equally spaced intervals are approximately 1 nanometer.

10. The method as recited in claim 8, wherein the equally spaced intervals are less than 1 nanometer.

11. The method as recited in claim 8, wherein the equally spaced intervals are greater than 1 nanometer.

12. The method as recited in claim 1, wherein each measurement of the second group of measurements is expressed as a number of counts for each sensor element.

13. The method as recited in claim 1, wherein the system response factor is expressed as a signal output amplitude of each of a plurality of discrete wavelengths of a full SPD.

14. The method as recited in claim 1, wherein the step of filtering uses an algorithm to isolate and identify source peaks of the first and second full SPDs.

15. The method as recited in claim 1, wherein the step of filtering uses an algorithm:

$$yi = xi - [1/16 \times \Sigma_{j=0}^{j=6} (4 - \tfrac{1}{2}j - 3\tfrac{1}{2}) \cdot x(i-(j-3))]$$

where y=one of the filtered data sets;
x=the other of the filtered data sets;
i=Index digit
to isolate and identify source peaks of the first and second full SPDs.

16. The method as recited in claim 1, wherein an algorithm implements a series of steps to smooth the filtered data sets to isolate and identify source peaks of the first and second full SPDs.

17. The method as recited in claim 1, wherein the step of aligning further includes the steps of:
shifting the second data set by a preselected increment;
interpolating the first data set by a wavelength offset;
determining an error between the shifted second data set and the interpolated first data set;
comparing the error against a preselected threshold;
repeating the steps above if the error is greater than the preselected threshold; and
determining an expression for an optimum shifted second data set and interpolated first data set if the error is less than the preselected threshold.

18. The method as recited in claim 1, wherein the first and second calibrated devices are each NIST-traceable wattmeters.

19. The method as recited in claim 1, wherein the calibration light source is a lamp selected from the group consisting of xenon, fluorescent, metal halide and mercury.

20. A method of exposing test specimens in a client accelerated weathering test apparatus to an accurate preselected level of irradiance, comprising the steps of:
determining a power level for generating a preselected level of irradiance from a light source based upon a type of light source filter assembly, a first data set for a calibrated light source including a first group of measurements from a first full spectrum power distribution ("SPD") and a desired irradiance level set point at a control wavelength from the light source;
determining a measured irradiance level from the light source based upon a second data set for the light source adjusted by a system response factor;
comparing the power level and the measured irradiance level at the control wavelength;
generating a light source power control signal; and
repeating the above steps at preselected intervals for a desired period of time.

21. The method as recited in claim 20, wherein the light source is a lamp selected from the group consisting of xenon, fluorescent, metal halide and mercury.

22. The method as recited in claim 20, wherein the calibrated light source is selected from the group consisting of xenon, fluorescent, metal halide and mercury.

23. The method as recited in claim 20, wherein the control wavelength is a range of wavelengths that may be used to determine photometric output.

24. The method as recited in claim 20, wherein the control wavelength is a range of wavelengths.

25. The method as recited in claim 20, wherein each measurement of the first group of measurements is expressed as a first irradiance amplitude for each of a plurality of discrete wavelengths at equally spaced intervals over the first full SPD.

26. The method as recited in claim 25, wherein the first group of measurements is enabled by a National Institute of Standards and Testing ("NIST")-traceable spectroradiometer.

27. The method as recited in claim 20, where in the second data set includes a second group of measurements from a second full SPD where each measurement of the second group of measurements is expressed as a number of counts for each sensor element.

28. The method as recited in claim 27, wherein the second group of measurements is enabled by a NIST-traceable spectroradiometer.

29. The method as recited in claim 28, wherein the spectroradiometer is a linear charge-coupled device.

30. An accelerated weathering test apparatus comprising:
a test chamber;
a test specimen mount for supporting test specimens in the test chamber;
a light source disposed within the test chamber for generating irradiance in the test chamber;
a controller for generating a light source power control signal based upon a plurality of inputs;

a power source responsive to the light source power control signal for outputting power to the light source; and a spectroradiometer for collecting a full spectrum power distribution ("SPD") of the light source, generating a data set representative of the full SPD and outputting the data set to the controller as one of the plurality of inputs.

31. The apparatus as recited in claim 30, wherein the spectroradiometer having a receiving optic device is disposed within the test chamber for direct interface with irradiance from the light source.

32. The apparatus as recited in claim 30, wherein a lightwave guide receiving optic device is disposed within the test chamber for direct interface with irradiance from the light source and channeling light from the light source to the spectroradiometer which is disposed remote from the test chamber.

33. The apparatus as recited in claim 32, wherein the receiving optic device is disposed on the test specimen mount.

34. The apparatus as recited in claim 32, wherein the receiving optic device is disposed in a test specimen plane defined by the test specimens supported by the test specimen mount.

35. The apparatus as recited in claim 30, wherein the data set includes a group of measurements from the full SPD where each measurement of the group of measurements is expressed as a number of counts for each sensor element.

36. The apparatus as recited in claim 30, wherein the light source is a lamp selected from the group consisting of xenon, fluorescent, metal halide and mercury.

37. The apparatus as recited in claim 30, wherein the spectroradiometer is a National Institute of Standards and Testing ("NIST")-traceable linear charge-coupled device.

38. The apparatus as recited in claim 30, wherein the controller determines a power level for generating a preselected level of irradiance from the light source based upon a type of light source filter assembly, a calibrated light source data set and a desired irradiance level set point of a control wavelength from the light source.

39. The apparatus as recited in claim 38, wherein the controller further determines a measured irradiance level from the light source based upon the data set for the light source adjusted by a system response factor.

40. The apparatus as recited in claim 39, wherein the controller compares the power level and the measured irradiance level, generates a light source power control signal and repeats the above steps at preselected intervals for a desired period of time.

41. The apparatus as recited in claim 30, wherein the controller includes a processing unit and memory that stores programming instructions that, when used by the processing unit, causes the controller to function to: determine a power level for generating a preselected level of irradiance from a light source based upon a type of light source filter assembly, a calibrated light source data set and a desired irradiance level set point for a control wavelength from the light source; determine a measured irradiance level from the light source based upon the data set for the light source adjusted by a system response factor; compare the power level and the measured irradiance level; generate a light source power control signal; and repeat the above steps at preselected intervals for a desired period of time.

* * * * *